United States Patent [19]

Brodeur et al.

[11] Patent Number: 5,814,730
[45] Date of Patent: Sep. 29, 1998

[54] MATERIAL CHARACTERISTIC TESTING METHOD AND APPARATUS USING INTERFEROMETRY TO DETECT ULTRASONIC SIGNALS IN A WEB

[75] Inventors: Pierre H. Brodeur, Smyrna; Yves H. Berthelot, Decatur; Joseph P. Gerhardstein, Atlanta; Mont A. Johnson, Snellville, all of Ga.

[73] Assignee: Institute of Paper Science and Technology and Georgia Institute of Technology, Atlanta, Ga.

[21] Appl. No.: 662,463

[22] Filed: Jun. 10, 1996

[51] Int. Cl.$^6$ .......................... G01N 29/08; G01N 29/24
[52] U.S. Cl. ................... 73/597; 73/643; 73/657; 73/159
[58] Field of Search .................. 73/159, 597, 598, 73/599, 600, 602, 617, 618, 639, 643, 644, 657; 162/198, 263; 356/429, 430, 431, 352, 358; 250/559.29; 364/471

[56] References Cited

U.S. PATENT DOCUMENTS

| | | | |
|---|---|---|---|
| 4,275,963 | 6/1981 | Primbsch | 356/35.5 |
| 4,622,853 | 11/1986 | Leugers | 73/597 |
| 4,633,715 | 1/1987 | Monchalin | 73/657 |
| 4,674,332 | 6/1987 | Pace et al. | 73/597 |
| 4,688,423 | 8/1987 | Orkosalo | 73/159 |
| 4,833,928 | 5/1989 | Luukkala et al. | 73/655 |
| 4,966,459 | 10/1990 | Monchalin | 73/657 |
| 5,025,665 | 6/1991 | Keyes et al. | 73/597 |
| 5,035,144 | 7/1991 | Aussel | 73/602 |
| 5,080,491 | 1/1992 | Monchalin et al. | 73/657 |
| 5,131,748 | 7/1992 | Monchalin et al. | 73/657 |
| 5,137,361 | 8/1992 | Heon et al. | 73/657 |
| 5,229,832 | 7/1993 | Gaynor | 356/360 |
| 5,361,638 | 11/1994 | Pattersson et al. | 73/159 |
| 5,398,538 | 3/1995 | Williams et al. | 73/159 |

*Primary Examiner*—Hezron E. Williams
*Assistant Examiner*—Rose M. Miller
*Attorney, Agent, or Firm*—Fitch, Even, Tabin & Flannery

[57] ABSTRACT

A non-destructive, non-contact testing apparatus and method which generally includes an ultrasonic signal generator for inducing one or more ultrasonic signals in a material and an optical interferometer that includes a laser for illuminating a section of the material and for detecting beat frequencies resulting from reflected light from the material. Deformations in the material as a result of the ultrasonic signal cause the beat frequency to be shifted as a result of the Doppler effect. Such differences in the beat frequency are detected by the system and used as an indication of a characteristic of the material.

38 Claims, 5 Drawing Sheets

MATERIAL CHARACTERISTIC TESTING METHOD AND APPARATUS USING INTERFEROMETRY TO DETECT ULTRASONIC SIGNALS IN A WEB

BACKGROUND OF THE INVENTION

1. Field of the Invention

This invention relates generally to a non-destructive and non-contact testing apparatus and method for determining various characteristics of a material, such as paper, and more particularly to a non-destructive and non-contact testing apparatus and method based upon optical interferometry in which lasers are used to detect ultrasonic signals in a web of material by detecting reflected beat frequencies from the web that are shifted due to the Doppler effect in the presence of an ultrasonic signal.

2. Description of the Prior Art

For many years paper manufacturers have utilized off-line testing methods to determine the various characteristics of a web of paper being manufactured. Because of the destructive nature of the testing, only random samples of the paper have been tested. Unfortunately, such random sampling can allow defective product to pass through undetected. As such, a significant amount of defective product may be made before the defect is detected and corrected, resulting in a significant amount of waste. Another disadvantage of such off-line testing is that it requires extra personnel and time, thereby adding to the cost to manufacture the web.

Because of the many disadvantages inherent in off-line testing techniques, instrumentation for on-line monitoring of various paper characteristics has received considerable interest during the last decade. However, many of the current on-line testing systems also have disadvantages. For example, such testing systems rely on physical contact between the transducers and the web for acoustic coupling, which although effective, is fairly complex and requires good and constant contact between the transducers and the web being tested.

In order to overcome the problems associated with such on-line testing systems, several non-contact on-line testing systems are known that obviate the above problems. In particular, hybrid systems are known whereby lasers are used to generate ultrasonic signals in a moving web, for example as disclosed in U.S. Pat. Nos. 5,361,638; 5,025,665; 4,674,332; and 4,622,853, hereby incorporated by reference. Such testing systems rely on measuring the time the ultrasonic signals take to pass a predetermined distance. Since the distance is known, the velocity of the ultrasonic signal can be determined. The problem with such systems is that the precise distance being monitored must be maintained, which is relatively difficult. Another disadvantage in such systems is that only the velocity of a wave traveling through the paper is detected, not the type of wave and its particular characteristics.

The technique of optical interferometry in which lasers are used has been described in the literature, as for example in U.S. Pat. No. 4,275,963 by Primbsch and U.S. Pat. No. 5,229,832 by Gaynor, but such technique has not heretofore been known or developed for application to continuous webs in paper manufacture. In particular, the mentioned technique has never been utilized in continuous moving webs of paper, as in paper manufacturing machines commonly used in the paper manufacturing industry.

SUMMARY OF THE INVENTION

Accordingly, it is an object of the present invention to provide a non-destructive and non-contact testing apparatus and method that uses optical interferometry to determine various characteristics of a material.

It is also an object of the present invention to provide a non-destructive and non-contact testing apparatus and method capable of testing continuously moving webs of various materials on-line without contacting the materials being tested.

Another object of the present invention is to provide a non-destructive and non-contact testing system which includes lasers for generating ultrasonic signals and detecting the resulting deformations in continuously moving webs of various materials by optical interferometry.

It is yet another object of the present invention to provide a non-destructive and non-contact testing apparatus which eliminates the need to maintain precise distances of the testing apparatus and which can accommodate fluctuations in distances experienced in paper manufacture.

Briefly, the present invention relates to a non-destructive, non-contact testing apparatus and method which generally includes an ultrasonic signal generator for inducing one or more ultrasonic signals in a material and an optical interferometer that includes a laser for illuminating a section of the material and for detecting beat frequencies resulting from reflected light from the material. Deformations in the material as a result of the ultrasonic signal cause the beat frequency to be shifted as a result of the Doppler effect. Such differences in the beat frequency are detected by the system and used as an indication of a characteristic, for example, specific stiffness, of the material on a continuous basis.

BRIEF DESCRIPTION OF THE DRAWINGS

These and other advantages of the present invention will become apparent from the following specification and drawings in which.

DETAILED DESCRIPTION OF THE INVENTION

Figure 1:
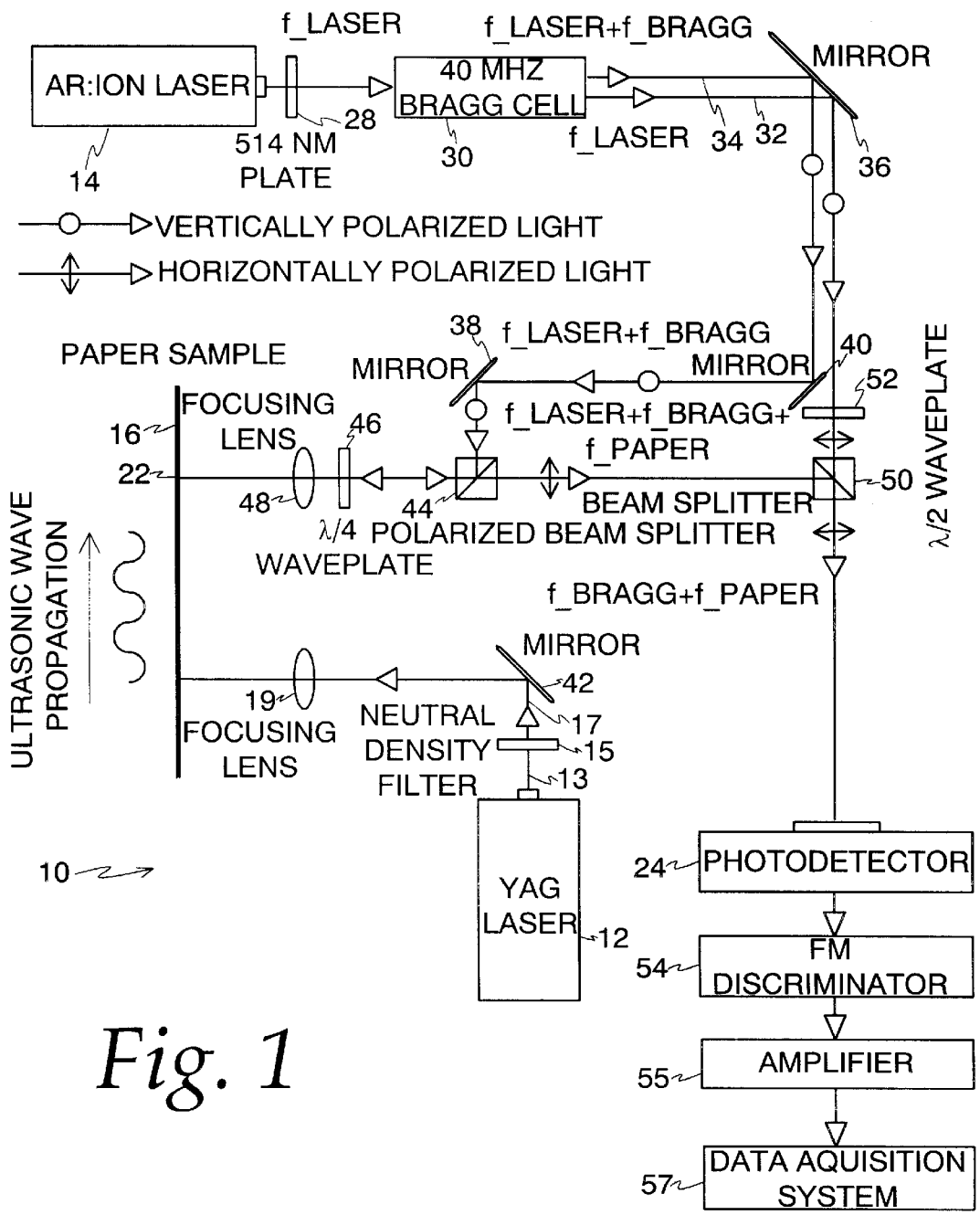
FIG. 1 is a schematic diagram of an out-of-plane asymmetric ($A_0$) system in accordance with one embodiment of the invention.
Figure 2:
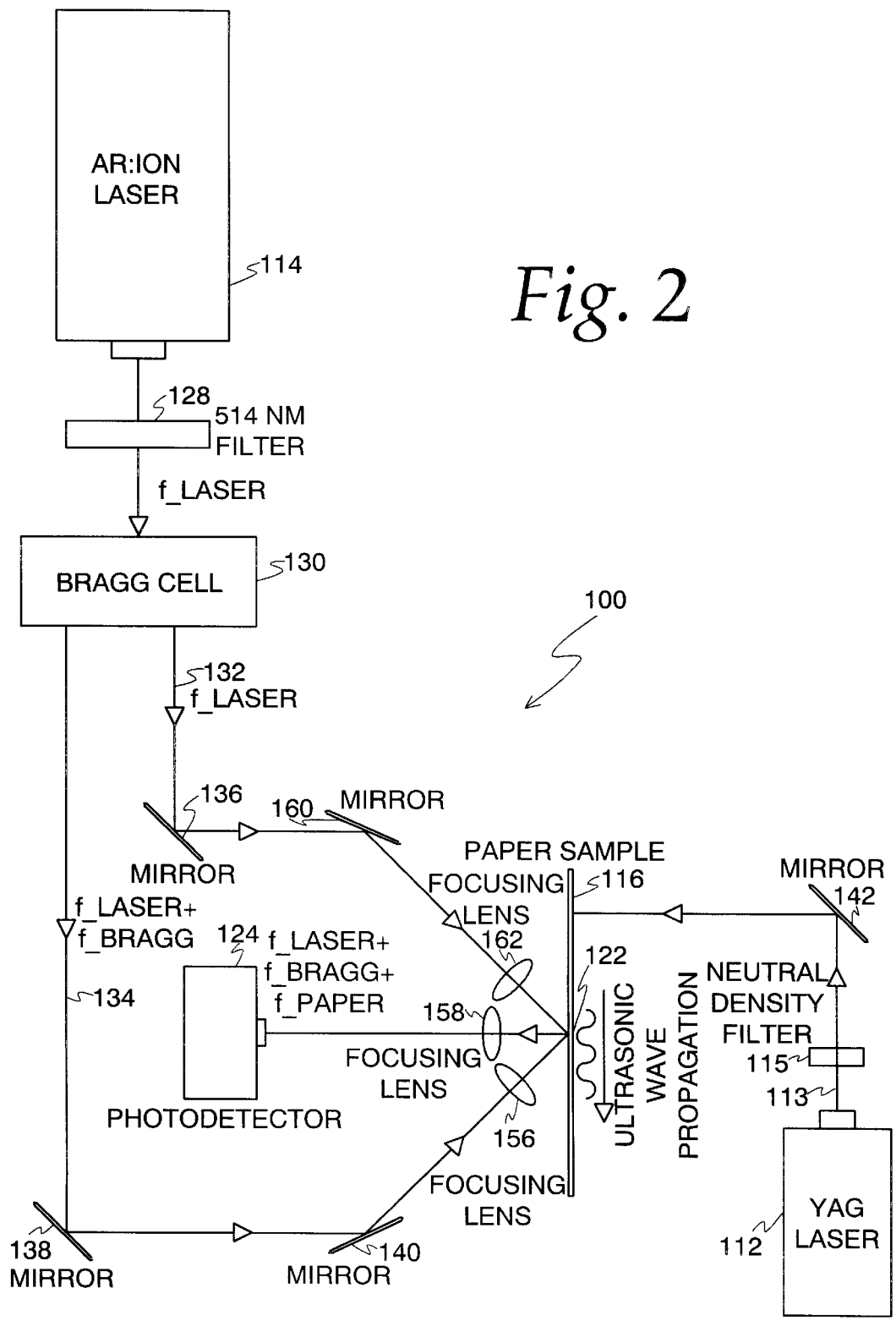
FIG. 2 is a schematic diagram of an in-plane symmetric ($S_0$) system in accordance with an alternate embodiment of the invention.
Figure 5:
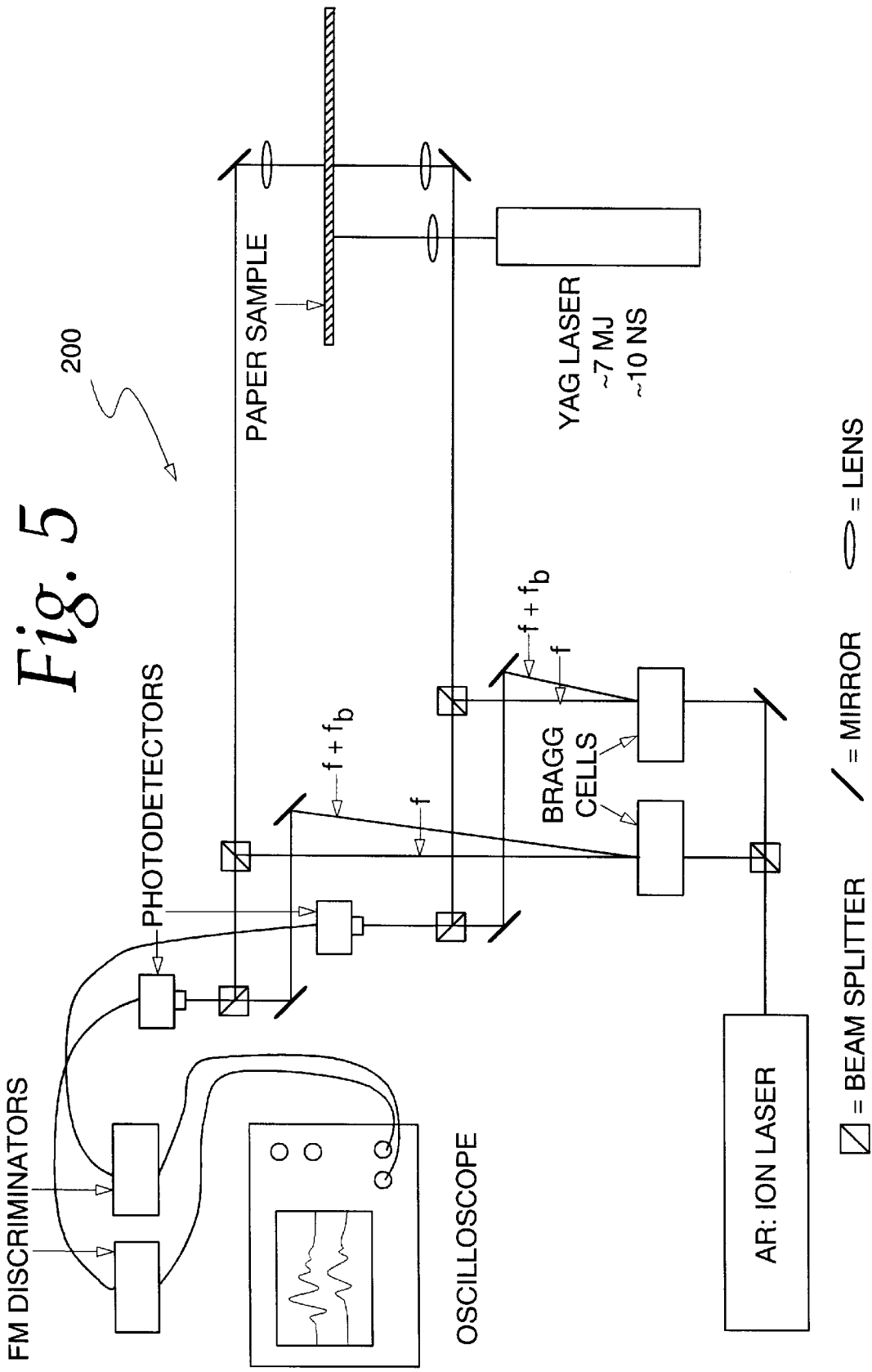
FIG. 5 is a schematic diagram of a combined in-plane and out-of-plane system in accordance with another alternate embodiment of the invention.

FIGS. 1 and 2 illustrate a non-destructive, non-contact interferometric testing apparatus for determining various properties of a web in accordance with two embodiments of the present invention as shown. The s.embodiments are particularly adapted to paper webs moving through conventional paper manufacturing machines. Both embodiments include an optical interferometer that detects changes in the beat frequency as a result of the Doppler effect resulting from an ultrasonic signal, thus obviating the need to maintain intimate or close-proximity contact with the web in the test apparatus as is required in other optical interferometric-type systems. In addition, as illustrated in FIG. 5, a third embodiment of the present invention is also contemplated, combining the first and second embodiments of the invention. Such combination allows efficiently measuring both symmetric and asymmetric waves simultaneously during the same test. The combined system allows for determining a broader range of paper characteristics than is possible using just a single testing system.

With specific reference to the first embodiment of an out-of-plane system, illustrated in FIG. 1, the apparatus 10 generally includes a device for inducing one or more ultrasonic signals in a moving web of paper, such as a time-varying laser 12 or acoustic ultrasonic signal inducing devices, such as a speaker or transducer, and an optical interferometer that includes a second laser 14.

The laser 12 may be either a CW or modulated laser, such as a Neodymium/Yttrium-Aluminum-Garnet ("YAG") laser 12. The second laser 14 may be an Ar:Ion laser.

With reference to FIG. 1, the ultrasonic signal inducing device, shown as a YAG laser 12, delivers short pulses of light (i.e. 4 ns of approximately 10 mJ energy at a repetition rate of about 1 Hz to a web 16), which results in ultrasonic signals being induced in the web 16 that cause deformations of the web 16. These induced ultrasonic signals, when induced in paper, are generally known as plate waves or Lamb waves. The waves are elastic, and consist of two types: asymmetric waves in which particle motions or oscillations are perpendicular to the surface of the web 16 and symmetric waves in which particle motions or oscillations are parallel to the surface of the web 16. To ensure that the amount of signal generation is non-destructive, the amount of energy absorbed by the web 16 may be controlled by first passing the beam through a neutral density filter 15. The filtered beam is then reflected off of a mirror and strikes the web perpendicular to its surface. To detect the Lamb waves in the web, an interferometer, which includes the laser 14, is used. In order to provide a source of monochromatic light, the beam from the laser 14 may be passed through a notch filter, for example, a 514.5 nm cut-on filter 28, although other filters of various other frequencies may also be used. This monochromatic light beam, identified as $f\_laser$, is then passed through an acousto-optic modulator, such as a 40 mHz Bragg cell 30, which shifts the frequency of the monochromatic light beam $f\_laser$ to a frequency equal to $f\_laser+f\_Bragg$ 34, where $f\_Bragg$ is the Bragg-shifted frequency. The Bragg cell 30 also splits the beam, so that the first half of the beam 32 exits unchanged (i.e. at a frequency $f\_laser$ 32) and is used as a reference frequency. Other beams of higher Bragg frequency multiples are blocked. The output beams 32, 34 from the Bragg cell 30 are vertically polarized. For the purpose of discussion only, beams 32 and 34 are defined as reference beam and detection beam, respectively. However, the beams may be interchanged, but will produce similar results. As further shown in FIG. 1, the Bragg-shifted beam 34 is reflected from several mirrors 36, 38 and 40 and reflected to a polarized beam splitter 44, which reflects a vertically polarized beam to a quarter wave plate 46, which circularly polarizes the beam. The beam 34 is then passed through an objective lens 48 which focuses the beam onto the web 16.

The beam 34 strikes the web 16 generally perpendicular to the plane of surface and is then reflected therefrom. The reflected light from the surface of the web 16 is collected by the objective lens 48 and reflected back through the quarter wave plate 46, which horizontally polarizes the reflected beam, to allow the beam 34 to pass through a polarized beam splitter 44. The horizontally polarized beam is directed toward a second beam splitter 50 and is combined with the beam 32, which acts as a reference beam. The recombined beam is then collected by the photodetector 24, which detects the beat frequencies of the combined beams. The output of the photodetector 24 is applied to an FM discriminator 54 that outputs a voltage signal that is proportional to the instantaneous surface velocity of the moving web, which can be integrated to provide the position of the sample as a function of time.

The laser 12 may be used to create an ultrasonic signal in the web 16, which causes Lamb waves to propagate through the web 16. More specifically, a beam 13 from the laser 12 is filtered by a neutral density filter 15 and reflected from a mirror 42 to cause a beam 17 to be reflected toward the web 16 in a direction generally perpendicular to the plane of the web 16. The beam 17 is focused by a focusing lens 19 and directed toward the web 16, thereby causing Lamb waves to travel through the web 16. When the Lamb waves cross the spot illuminated by the laser beam 14, the frequency of the beam 34 is shifted by a frequency $f\_paper$ as a result of the Doppler effect caused from the passing wave. As such, the beam 34 will have a frequency equal to $f\_laser+f\_Bragg+f\_paper$ in the presence of a Lamb wave. If no wave is detected, the frequency of the beam 34 will be equal to $f\_laser+f\_Bragg$.

More particularly, after the beam 34 is reflected from the surface of the web 16 and combined with the reference beam 32 in the beam splitter 50, the difference in frequency between the two beams causes constructive and destructive interference (interferometry) to occur in the combined beam, which creates a beat frequency equal to the difference in the frequencies of the two beams. When no Lamb wave is present in the web 16, the beat frequency will be $f\_Bragg$. When a Lamb wave is present in the web 16, the reflected beam, as discussed above, is shifted by the Doppler effect, which results in a beat frequency equal to $f\_Bragg+f\_paper$, where $f\_paper$ is the Doppler-shifted frequency caused by the motion or oscillation in the web 16 due to propagating Lamb waves.

Figure 3:
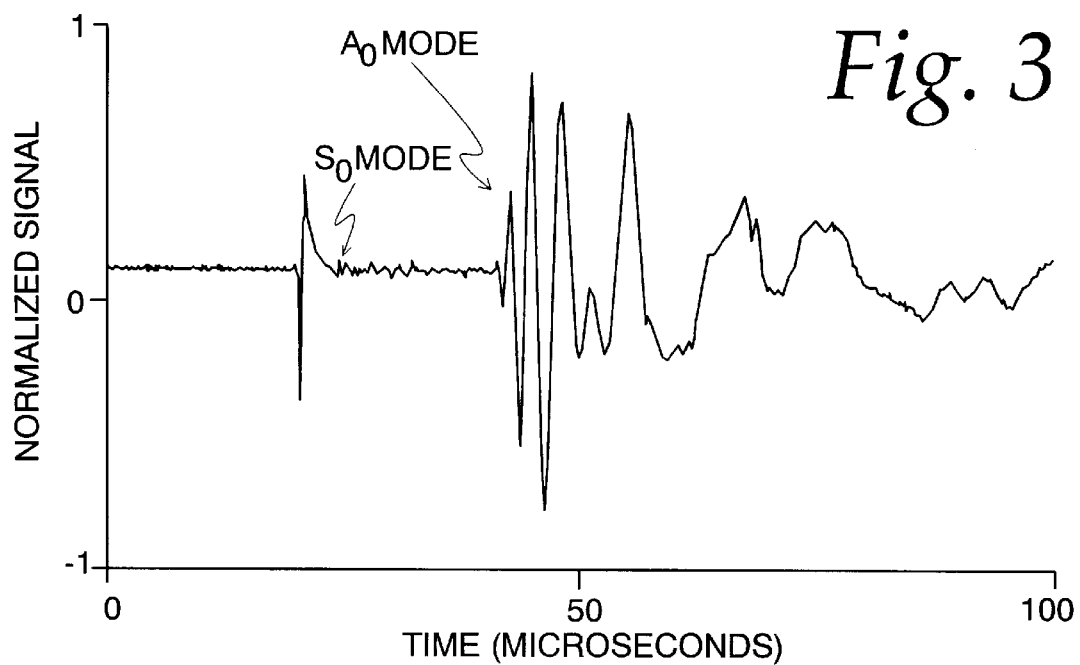
FIG. 3 is a graphical illustration of the exemplary output data of the system illustrated in FIG. 1.

The recombined beam is then collected by a photodetector 24 which measures the light intensity, and is also capable of measuring variations in intensity. The output of the photodetector 24 is applied to FM discriminator 54, set such that an input of $f\_Bragg$ gives an output of zero volts, as is the case when there is no detected Lamb wave in the web. Hence, when a signal enters the FM discriminator with the frequency of $f\_Bragg+f\_paper$, the output is a voltage signal proportional to $f\_paper$. This voltage signal can be related to the perpendicular velocity of the web, in both the machine direction (MD) and cross-machine direction (CD), under the spot illuminated by the laser, which, in turn, can be integrated to provide the position of the web as a function of time. As shown in FIG. 3, which represents a graphical illustration of exemplary data collected by the data acquisition system 57 for plain white copy paper, the out-of-plane system is particularly sensitive to asymmetric waves $A_o$, which are motions perpendicular to the surface of the web. Motions parallel to the surface of the web (i.e. symmetric waves) are detectable but relatively weak when compared to asymmetric waves.

The output voltage from the FM Discriminator 54 may be amplified by an amplifier 55 and applied to a data acquisition system 57.

Referring now to FIG. 2, directed to an in-plane system, an apparatus 100 in accordance with an alternative embodiment of the present invention is shown for an in-plane detector. As shown in FIG. 2, the ultrasonic signal inducing device, for example, a YAG laser 112, delivers short pulses of light as discussed above. To detect the ultrasonic signal 118, or Lamb waves, as mentioned above, of the web 116, an interferometer that includes an Ar:Ion laser 114 is used. The beam from the laser 114 is passed through a notch filter 128 to produce a monochromatic beam of light having a wavelength $f\_laser$ of, for example, a 514.5 nm. The monochromatic beam is then passed through an acousto-optic modulator, such as a Bragg cell that shifts the frequency of the beam and also splits the beam, so that the first half of the beam 132 exits unchanged and can be used to act as a reference frequency. The second half of the beam 134 exits the Bragg cell 130 at a frequency of the laser beam frequency $f\_laser$ plus the Bragg cell frequency $f\_Bragg$. Other beams of higher Bragg frequency multiples are blocked. As shown in FIG. 2, both the Bragg shifted and the unmodulated beams are steered around by mirrors 132, 138, 140, 160 and then aimed at the same spot 122 on the web 116, such that they impact the web at an acute angle, for example, a 45° angle, relative to the surface of the web and 180 degrees apart longitudinally. Objective lenses 156 and 162 are used to focus the incoming beams to the same spot on the surface of the web 116. The beams strike the web 116 and are recombined and collected by an objective lens 158. The recombined beam is then collected by the photodetector 124. The output of the photodetector 124 is applied to an FM discriminator (not shown) that outputs a voltage signal proportional to the frequency of the ultrasonic signal propagating in the tested material.

In operation, when an ultrasonic signal, or Lamb wave, travels through the web 116, it creates deformations in the web 116 which cross the spot illuminated by the laser beam 122, which, in turn, shifts the frequency of the beam by $f\_paper$ as a result of the Doppler shift from the passing deformation in the web caused by the Lamb waves. The interference between the reflections of the two lasers creates a beat pattern frequency equal to $f\_Bragg + f\_paper$. The beam, after reflecting off the web 116, is passed through a focusing lens 158 and then collected by the photodetector 124 which measures the beat frequency. The output of the photodetector 124 is applied to an FM discriminator (not shown), that is set such that an input of $f\_Bragg$ gives an output of zero volts, as is the case when there is no detected Lamb wave in the web. Hence, when a signal enters the FM discriminator with the frequency of $f\_Bragg + f\_paper$, the output is a voltage signal proportionate to $f\_paper$. This voltage signal can be related to the velocity of the web, along both MD and CD, under the spot illuminated by the laser, which, in turn, can be integrated to provide position.

Figure 4:
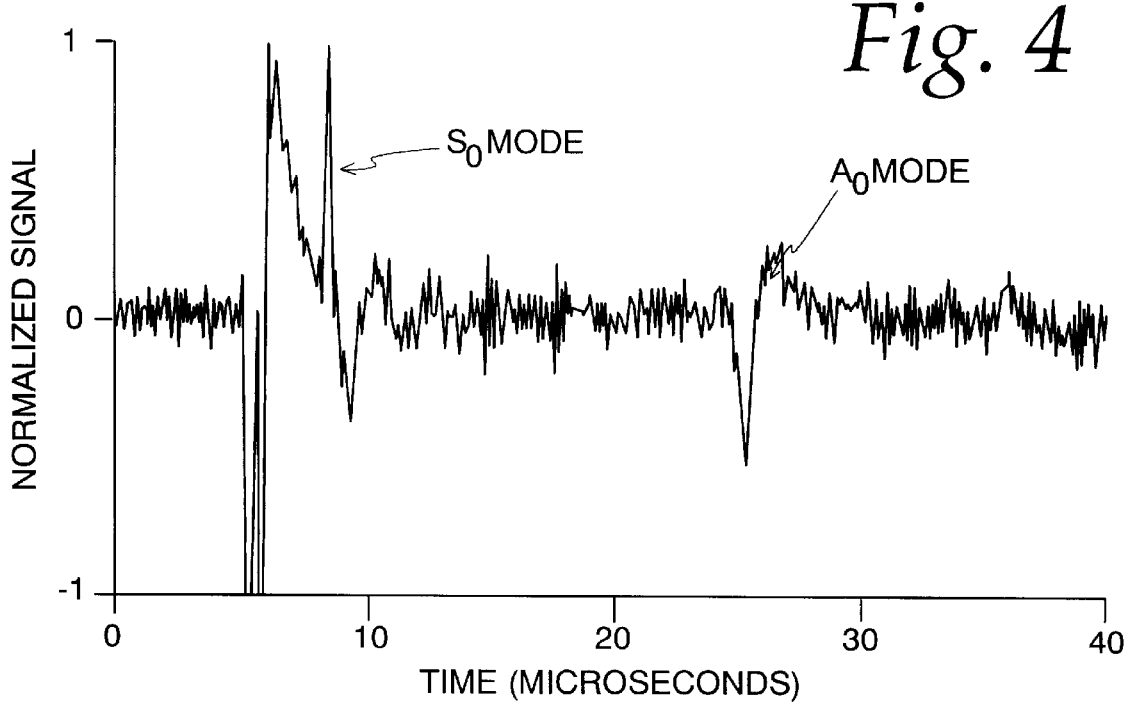
FIG. 4 is similar to FIG. 3 but for the system illustrated in FIG. 2.
Figure 6:
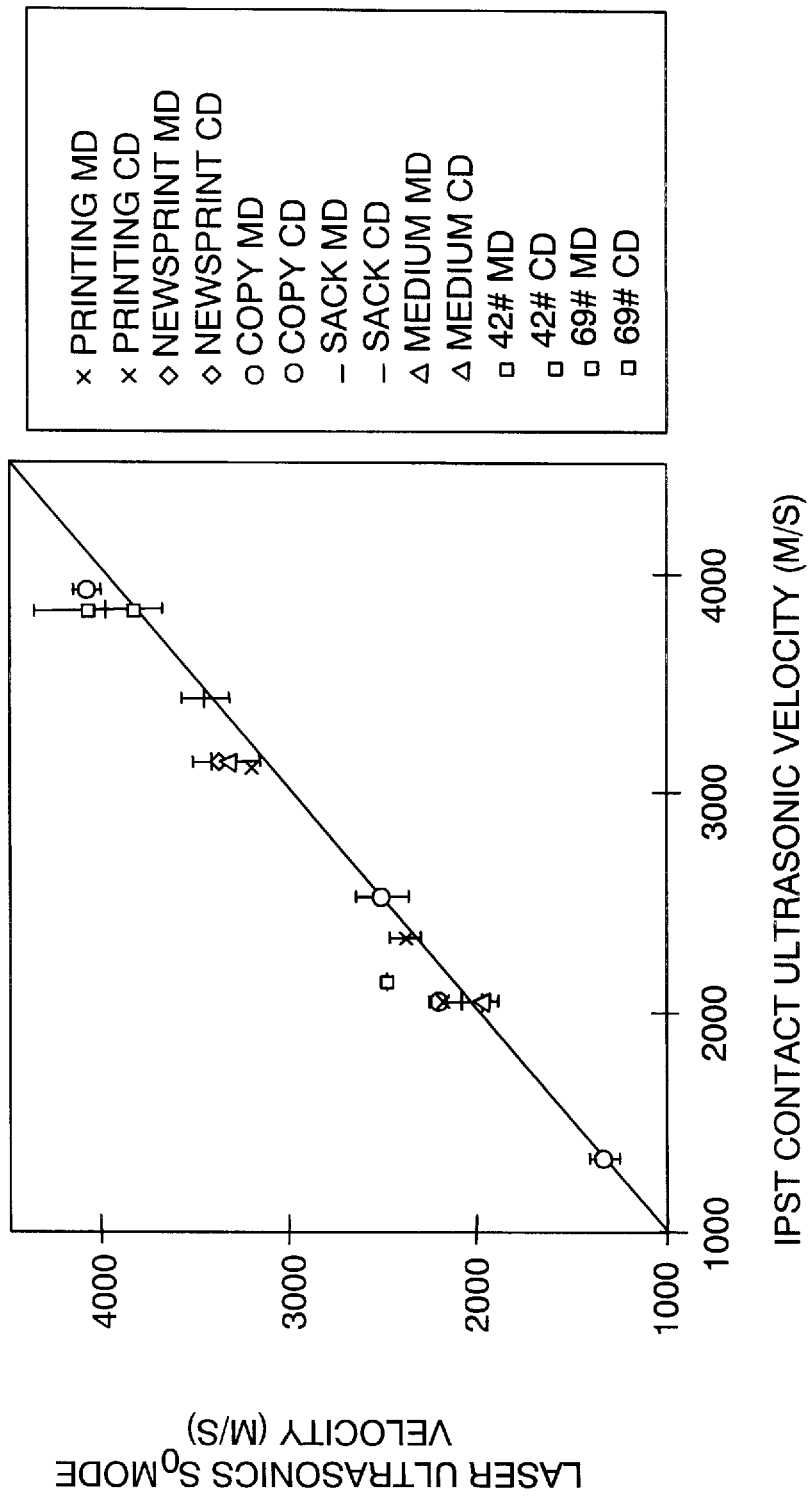
FIG. 6 is a graph of laser-ultrasonics $S_0$ mode velocity versus contact velocity for several different grades of paper.

As discussed above, the output of the photodetector may be amplified and collected by a data acquisition system (not shown). Referring to FIG. 4, exemplary data for plain, white copy paper is illustrated. It must be emphasized, however, that white copy paper is used by way of example only. Other grades of papers may be used with similar results (FIG. 6). As shown, the in-plane system is most sensitive to motions parallel to the surface (i.e., symmetric waves $S_0$), and displacements perpendicular to the surface (i.e., asymmetric waves), although detectable, are relatively weak when compared to symmetric waves.

Referring to FIG. 5, an apparatus 200 is shown in accordance with a third embodiment of the present invention. As shown in FIG. 5, the in-plane and the out-of-plane detection methods may be combined in a single apparatus to provide simultaneous measurements of both asymmetric and symmetric mode Lamb waves. By measuring the phase velocity and frequency of the Lamb waves propagating in the moving paper web, a determination can be made as to which of the possible modes, either $A_0$ or $S_0$, are detected. The velocity information from each mode may then be used to predict the values of the elastic stiffness constants of the web being sampled. In particular, it is known that approximated values of the specific stiffnesses $$\frac{C_{11}}{\rho}$$

and $$\frac{C_{22}}{\rho},$$

where $\rho$ is the density of the material, are obtained by $S_0$ phase velocity along MD and CD, respectively. For example, $$\frac{C_{11}}{\rho} = V^2_{S_0 MD}$$

and $$\frac{C_{22}}{\rho} = V^2_{S_0 CD}$$

where $$V^2_{S_0 MD}$$

and $$V^2_{S_0 CD}$$

are the square of the $S_0$ mode velocities along MD and CD, respectively. It is also believed that approximated values of the specific stiffnesses $$\frac{C_{55}}{\rho}$$

and $$\frac{C_{44}}{\rho}$$

may be obtained in a manner similar to that described above, using $A_0$ phase velocity along MD and CD.

Those skilled in the art can now appreciate from the foregoing description that the broad teachings of the present invention can be implemented in a variety of forms. Therefore, while this invention has been described in connection with particular examples thereof, the true scope of the invention should not be so limited since other modifications will become apparent to the skilled practitioner upon a study of the drawings, specification and following claims.

What is claimed is:

1. A method for measuring ultrasonic vibrations in a moving paper web in a production line, comprising the steps of:

moving a paper web in a machine direction through a production line making the paper web;

inducing an ultrasonic vibration at a first location on the paper web;

providing a first laser beam having a reference frequency;

illuminating said paper web at a second location adjacent said first location with a second laser beam having a frequency differing from said reference frequency by a preselected frequency;

combining said first laser beam with a reflection from said second location of said second laser beam to provide a combined beam, said paper web reflecting the second laser beam to provide a reflected second laser beam, the second reflected laser beam having a frequency which is Doppler shifted from the first laser beam having the reference frequency by virtue of the paper web moving substantially perpendicular to the plane of the paper web along the path of the second beam;

detecting a beat frequency in said combined beam, the beat frequency being responsive to the Doppler shift in the second reflected laser beam; and determining the Doppler shift from the beat frequency caused by the ultrasonic vibration to determine a characteristic of the paper web.

2. A method according to claim 1, wherein said determining step comprises the steps of:

providing a frequency modulation (FM) discriminator which produces an output signal of zero when an input signal is modulated at said preselected signal;

inputting said combined beam to said FM discriminator; and measuring deviations from zero of the output of said FM discriminator in response to said combined beam to provide an indication of said Doppler shift in said reflection frequency.

3. An apparatus for non-contact testing of a paper web moving in the machine direction in a production line for the web, the apparatus comprising;

a first source for directing at a first location on said paper web a laser pulse sufficient to induce ultrasonic signals in said web;

a second source for providing a laser beam having a reference frequency;

a third source for illuminating a second location on said paper web with a laser beam having a shifted frequency equal to said reference frequency plus a preselected frequency;

means for combining said reference laser beam with a reflection of said shifted laser beam from said second location;

means responsive to said combined beam for determining a beat frequency of a beat modulation therein; and a discriminator for producing an output proportional to the difference between said beat frequency and said preselected frequency which output is effective for measuring a characteristic of the paper web.

4. An apparatus according to claim 3, wherein said beat frequency determining means comprises a photodetector disposed to produce an output voltage proportional to the intensity of said combined beam.

5. An apparatus according to claim 4 further comprising:

data acquisition means for recording the discriminator output as a function of time.

6. An apparatus according to claim 5 further comprising means for determining the speed of propagation of said ultrasonic signals in said web in response to a combination of the pulsing of said first source, and the output of said discriminator.

7. An apparatus according to claim 6 further comprising calculation means for providing the specific stiffness of said web in response to said determination of the speed of propagation of said ultrasonic signals by said speed determining means.

8. A method for determining a characteristic of a paper web moving in a production line, comprising:

moving a paper web in a machine direction through a production line making the paper web;

inducing an ultrasonic vibration at a first location on the paper web with an excitation laser beam, which ultrasonic vibration propagates through the paper web outward from said first location;

illuminating said paper web at a second location at a distance from said first location with an incident laser beam having a first frequency;

combining a reference laser beam having a second frequency differing from said first frequency by a preselected frequency, with a reflection from said second location of said incident laser beam to provide a combined beam, said paper web reflecting the incident laser beam to provide a reflected laser beam having a frequency which is Doppler-shifted in proportion to a velocity of the paper web normal to the paper web surface caused by the ultrasonic vibration propagating through the paper web;

detecting a beat frequency in said combined beam, the beat frequency being responsive to the Doppler shift in the reflected laser beam; and producing a signal in response to a difference between said beat frequency and said preselected frequency, indicative or the Doppler shift caused by the ultrasonic vibration, to determine a characteristic of the paper web.

9. A method according to claim 8, wherein said signal-producing step comprises:

providing a frequency modulation discriminator which produces an output signal having a null value when an input signal is modulated at said preselected signal;

inputting said combined beam to said frequency modulation discriminator; and detecting deviations from said null value of the output signal from said frequency modulation discriminator in response to said combined beam to provide an indication of said Doppler shift in said reflected laser beam frequency, which is indicative of the ultrasonic vibration.

10. A method according to claim 9, further comprising:

amplifying said output signal from the frequency modulation discriminator;

acquiring said amplified frequency modulation discriminator output signal over time, to provide first information regarding the velocity of the paper web in a direction normal to the paper web over time, caused by a packet of propagating ultrasonic waves comprising asymmetric and symmetric modes of said ultrasonic vibration.

11. A method according to claim 10, further comprising integrating with respect to time said frequency modulation discriminator output signal, to provide second information regarding the displacement of the paper web in a direction normal to the paper web, caused by a packet of propagating ultrasonic waves comprising asymmetric and symmetric modes of said ultrasonic vibration.

12. A method according to claim 11, wherein said reference laser beam is provided by an argon ion laser.

13. A method according to claim 12, wherein said excitation laser beam provides pulses of laser light at a repetition rate of about 1 Hertz, each pulse having a duration of about 4 nanoseconds and delivering about, 10 milliJoules of energy.

14. A method according to claim 13, wherein said incident laser beam is provided by passing at least a portion of said reference laser beam through a Bragg cell disposed to output a laser beam having a frequency shifted from said reference frequency by about 40 Megahertz.

15. A method according to claim 9, further comprising:

providing a second reference laser beam having a second reference frequency;

illuminating said paper web at a third location at a distance from said first location, with a second incident laser beam having a frequency differing from said second reference frequency by a second preselected frequency;

combining said second reference laser beam with a reflection from said third location of said second incident laser beam to provide a second combined beam, said paper web reflecting the second incident laser beam to provide a second reflected laser beam having a frequency which is Doppler-shifted in proportion to a velocity of the paper web normal to the paper web surface caused by the ultrasonic vibration propagating through the paper web;

detecting a second beat frequency in said second combined beam, the second beat frequency being responsive to the Doppler shift in the second reflected laser beam;

producing a signal proportional to a difference between said second beat frequency and said second preselected frequency, said difference being indicative of the Doppler shift caused by the ultrasonic vibration;

providing a second frequency modulation discriminator which produces an output signal having a null value when an input signal is modulated at said second preselected signal;

inputting said second combined beam to said second frequency modulation discriminator; and detecting deviations from said null value of the output signal from said second frequency modulation discriminator in response to said second combined beam to provide an indication in said second reflected laser beam frequency of the Doppler shift caused by the ultrasonic vibration, to determine a characteristic of the paper web.

16. A method according to claim 15, wherein said second location is separated from said first location in said machine direction, and said third location is separated from said first location in a cross-machine direction which is orthogonal to the machine direction.

17. A method according to claim 9, wherein illuminating said paper web at said second location with said incident laser beam comprises directing said incident laser beam at said second location at an incident angle substantially oblique with respect to a direction normal to the paper web.

18. A method according to claim 15, wherein one of the set of the actions of illuminating said paper web at said second location with said incident laser beam and illuminating said paper web at said third location with said second incident laser beam, comprises illuminating at an incident angle substantially oblique with respect to a direction normal to the paper web.

19. A method according to claim 10, further comprising:

recording when said excitation laser beam begins inducing the ultrasonic vibration;

determining from said first information a symmetric mode phase velocity in the machine direction; and determining the specific stiffness $C_{11}$ of the paper web in response to the determination of said machine direction symmetric mode phase velocity.

20. A method according to claim 10, further comprising:

recording when said excitation laser beam begins inducing the ultrasonic vibration;

determining from said first information an asymmetric mode phase velocity in the machine direction; and determining the specific stiffness $C_{55}$ of the paper web in response to the determination of said machine direction asymmetric mode phase velocity.

21. A method according to claim 16, further comprising:

amplifying said output signal from the second frequency modulation discriminator;

acquiring said second amplified frequency modulation discriminator output signal over time to provide third information regarding the velocity of the paper web in a direction normal to the paper web over time, caused by a packet of propagating ultrasonic waves comprising asymmetric and symmetric modes of said ultrasonic vibration;

recording when said excitation laser beam begins inducing the ultrasonic vibration;

determining from said third information a symmetric mode phase velocity in the cross-machine direction; and determining the specific stiffness $C_{22}$ of the paper web in response to the determination of said cross-machine direction symmetric mode phase velocity.

22. A method according to claim 16, further comprising:

amplifying said output signal from the second frequency modulation discriminator;

acquiring said second amplified frequency modulation discriminator output signal over time to provide third information regarding the velocity of the paper web in a direction normal to the paper web over time, caused by a packet of propagating ultrasonic waves comprising asymmetric and symmetric modes of said ultrasonic vibration;

recording when said excitation laser beam begins inducing the ultrasonic vibration;

determining from said third information an asymmetric mode phase velocity in the cross-machine direction; and determining the specific stiffness $C_{44}$ of the paper web in response to the determination of said cross-machine direction asymmetric mode phase velocity.

23. An apparatus according to claim 4, further comprising:

an amplifier for receiving said discriminator output and providing an amplified discriminator output; and a data acquisition system responsive to said amplified discriminator output for providing a phase velocity of at least one of the set of a symmetric mode of said ultrasonic signals and an asymmetric mode of said ultrasonic signals, effective to determine a specific stiffness of said paper web.

24. An apparatus according to claim 23, wherein said third source is a Bragg cell disposed to receive at least a portion of said reference frequency laser beam and provide a laser beam having a frequency shifted from said reference frequency by about 40 Megahertz.

25. An apparatus according to claim 4, further comprising:

a fourth source for providing a laser beam having a second reference frequency;

a fifth source for illuminating a third location on said web with a laser beam having a second shifted frequency equal to said second reference frequency plus a second preselected frequency;

second combining means for combining said second reference laser beam with a reflection of said second shifted laser beam from said third location to provide a second combined beam;

a second photo detector disposed to produce an output voltage proportional to the intensity of said second combined beam, said output voltage having a second beat frequency produced by interference between said second reference frequency and said second reflected frequency;

a second discriminator responsive to the output voltage of said second photo detector for producing an output proportional to the difference between said second beat frequency and said second preselected frequency, which output is effective for measuring a characteristic of the paper web.

26. An apparatus according to claim 25, wherein said second location is separated from said first location in said machine direction, and said third location is separated from said first location in a cross-machine direction which is orthogonal to the machine direction.

27. An apparatus according to claim 26, wherein at least one of the set of said third source and said fifth source is disposed to illuminate at an incident angle substantially oblique with respect to a direction normal to the paper web.

28. An apparatus according to claim 4, wherein said third source is disposed to illuminate: the paper web at said second location at an incident angle substantially oblique with respect to a direction normal to the paper web.

29. An apparatus according to claim 24, wherein said first source comprises a YAG laser disposed to deliver pulses of laser light at a repetition rate of about 1 Hertz, each pulse having a duration of about 4 nanoseconds and delivering about 10 milliJoules of energy.

30. An apparatus according to claim 29, wherein said second source comprises an argon ion laser.

31. An apparatus according to claim 30, wherein said Bragg cell outputs both said reference laser beam and said shifted laser beam with a matching vertical polarization, further comprising:

a half-wave plate disposed between said Bragg cell and said combining means;

a polarized beam splitter, disposed to reflect said vertically-polarized shifted laser beam toward said second location, and disposed to transparently pass any horizontally polarized laser light reflected from said second location toward said combining means; and a quarter-wave plate disposed between said second location and said polarized beam splitter.

32. An apparatus according to claim 25, wherein said second location and said third location are on opposite sides of the paper web.

33. An apparatus for non-contact determination of a characteristic of a paper web moving in a machine direction in a production line for the web, the apparatus comprising:

an excitation laser source for illuminating the paper web at a first location with sufficient energy to induce ultrasonic-frequency vibrations in the web which propagate outward from said first location;

a laser heterodyne interferometer disposed to produce an interference laser signal from laser illumination of a second location on the web;

a photo detector for producing an intensity signal in response to said interference laser signal;

a frequency modulation discriminator for producing an output signal in response to frequency modulation in said intensity signal, said output signal relating to Doppler shifting of said laser illumination of said interferometer caused by a velocity of the web normal to the surface of the web, imparted by said ultrasonic vibrations; and a data processing system for determining a characteristic of the web in response to said output signal.

34. An apparatus according to claim 33, further comprising:

a second laser heterodyne interferometer disposed to produce a second interference laser signal from laser illumination of a third location on the web;

a second photo detector for producing a second intensity signal in response to said second interference laser signal; and a second frequency modulation discriminator for producing a second output signal to said data processing system in response to frequency modulation in said second intensity signal, said second output signal relating to Doppler shifting of said laser illumination of said second interferometer caused by a velocity of the web normal to the surface of the web, imparted by said ultrasonic vibrations.

35. An apparatus according to claim 34, wherein said second location and said third location are on opposite sides of the web.

36. An apparatus according to claim 34, wherein said second location is separated from said first location in the machine-direction, and said third location is separated from said first location in a cross-machine direction which is orthogonal to the machine-direction.

37. An apparatus according to claim 36, wherein said data processing system is disposed to compute a phase velocity of an asymmetric mode of said ultrasonic vibrations in the web.

38. An apparatus according to claim 36, wherein said data processing system is disposed to compute a phase velocity of a symmetric mode of said ultrasonic vibrations in the web.

* * * * *